United States Patent
Karadeolian et al.

(10) Patent No.: US 11,046,638 B2
(45) Date of Patent: Jun. 29, 2021

(54) PROCESSES FOR THE PREPARATION OF ZUCLOMIPHENE AND INTERMEDIATES THEREOF

(71) Applicant: Apotex Inc., Toronto (CA)

(72) Inventors: Avedis Karadeolian, Brantford (CA); Fabio E. S. Souza, Brantford (CA); Michael R. Emmett, Brantford (CA); Allan W. Rey, Brantford (CA)

(73) Assignee: Apotex Inc., Ontario (CA)

( * ) Notice: Subject to any disclaimer, the term of this patent is extended or adjusted under 35 U.S.C. 154(b) by 0 days.

(21) Appl. No.: 17/095,707

(22) Filed: Nov. 11, 2020

(65) Prior Publication Data

US 2021/0147337 A1 May 20, 2021

Related U.S. Application Data

(60) Provisional application No. 62/935,107, filed on Nov. 14, 2019.

(51) Int. Cl.
*C07C 213/02* (2006.01)
*B01J 23/755* (2006.01)
*C07C 217/60* (2006.01)

(52) U.S. Cl.
CPC ........ *C07C 213/02* (2013.01); *B01J 23/755* (2013.01); *C07C 217/60* (2013.01)

(58) Field of Classification Search
None
See application file for complete search history.

(56) References Cited

U.S. PATENT DOCUMENTS

| | | | |
|---|---|---|---|
| 2,914,563 | A | 11/1959 | Allen et al. |
| 3,848,030 | A | 11/1974 | Viterbo et al. |
| 9,428,442 | B2 | 8/2016 | Serafini et al. |
| 9,913,815 | B2 | 3/2018 | Steiner et al. |
| 9,914,696 | B2 | 3/2018 | Podolski et al. |
| 2015/0202167 | A1 | 7/2015 | Podolski et al. |

FOREIGN PATENT DOCUMENTS

| | | |
|---|---|---|
| FR | 3082842 A1 | 12/2019 |
| GB | 1099093 | 1/1968 |
| WO | 2014031177 A1 | 2/2014 |
| WO | 2016014812 A1 | 1/2016 |
| WO | 2016106189 A1 | 6/2016 |

OTHER PUBLICATIONS

Wilger etal. J. Org. Chem. 2019, 84, 11612-11622.*
Al-Hassan, "Synthesis of Clomid Using Palladium-Catalyzed Cross-Coupling", Synthetic Communications, 1987, pp. 1787-1796, vol. 17, No. 15.
Bernstein, "Polymorphism in Molecular Crystals", Oxford University Press, 2002, 4 pages, New York, USA.
Crenshaw et al., "Synthesis of Trisubstituted Vinyl Chlorides", Journal of Organic Chemistry, 1983, pp. 2782-2784, vol. 48, No. 16.
Dolginova et al., "Synthesis and Biological Study of the cis- and trans-Isomers of Clomiphene Citrate and Some Intermediates of its Synthesis", Plenum Publishing Corporation, 1985, pp. 758-764.
Palopoli et al., "Substituted Aminoalkoxytriarylhaloethylenes", Journal of Medicinal Chemistry, 1967, pp. 84-86, vol. 10, No. 1.
Porter, "Coating of Pharmaceutical Dosage Forms", Remington The Science and Practice of Pharmacy 21st Edition, 2006, Chapter 46, pp. 929-938, Lippincott Williams & Wilkins, Philadelphia, USA.
Rudnic et al., "Oral Solid Dosage Forms", Remington The Science and Practice of Pharmacy 21st Edition, 2006, Chapter 45, pp. 889-928, Lippincott Williams & Wilkins, Philadelphia, USA.
Stahl et al., "Handbook of Pharmaceutical Salts Properties, Selection, and Use", International Union of Pure and Applied Chemistry (IUPAC), 2002, 18 pages.
"Veru Announces Positive Top-Line Interim Data from Phase 2 Clinical Trial of Zuclomiphene to Treat Hot Flashes in Men with Prostate Cancer on Androgen Deprivation Therapy", Jan. 13, 2020, 5 pages, retrieved from https://verupharma.com/news/.

* cited by examiner

*Primary Examiner* — Clinton A Brooks
(74) *Attorney, Agent, or Firm* — The Webb Law Firm

(57) ABSTRACT

The present invention provides processes for the preparation of zuclomiphene, as well as intermediates useful in the preparation thereof. In particular, processes are provided for the carbometallation of diphenylacetylene with a compound of Formula (3) to afford either zuclomiphene or an intermediate which is converted to zuclomiphene.

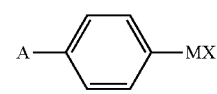

(3)

17 Claims, No Drawings

PROCESSES FOR THE PREPARATION OF ZUCLOMIPHENE AND INTERMEDIATES THEREOF

CROSS-REFERENCE TO RELATED APPLICATION

This application claims the benefit of U.S. Provisional Patent Application No. 62/935,107, filed Nov. 14, 2019, the disclosure of which is hereby incorporated by reference in its entirety.

TECHNICAL FIELD

The present invention relates to processes for the preparation of zuclomiphene and to intermediates used in the preparation thereof.

BACKGROUND

Clomid®, a drug initially approved by the United States Food and Drug Association in 1967 as an ovulatory stimulant, is an isomeric mixture of the citrate salts of cis-clomiphene (Z-clomiphene or 'zuclomiphene', (1-A)) and trans-clomiphene (E-clomiphene or 'enclomiphene', (1-B)) containing between 30% and 50% of the cis-isomer. Pure cis-isomer zuclomiphene (1-A), or (2-[4-[(Z)-2-chloro-1,2-diphenylethenyl]phenoxy]-N,N-diethylethanamine), in the form of the citrate salt, is currently undergoing evaluation in clinical trials in the United States to treat hot flashes experienced by male patients with advanced prostate canner undergoing androgen deprivation therapy (ADT).

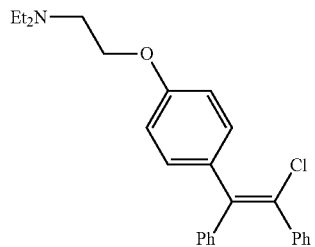

(1-A)

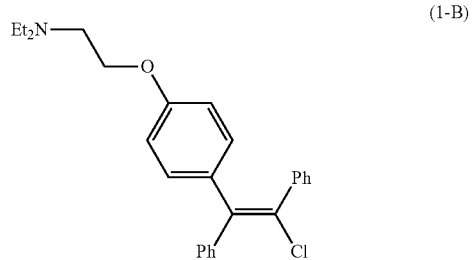

(1-B)

A process for the preparation of a series of substituted aminoalkoxytriarylhaloethylenes, which includes clomiphene, is disclosed in Palopoli et a. *J. Med. Chem.* 1967, 10 (1), 84-6, which is depicted in Scheme 1. Triarylethylene (D) is obtained by reaction of benzylmagnesium bromide (B) with aminoethoxy-substituted diphenyl ketone (A), followed by dehydration of alcohol (C). Chlorination of triarylethylene (D) using a solution of chlorine in carbon tetrachloride followed by salt formation with citric acid affords an unspecified ratio of clomiphene isomers (1) as dihydrogen citrate salts. Further conversion of the isomeric salt mixture to the corresponding hydrochloride salts followed by repeated fractional crystallization affords isolated isomers zuclomiphene (1-A) hydrochloride and enclomiphene (1-B) hydrochloride.

Scheme 1 (Prior Art)

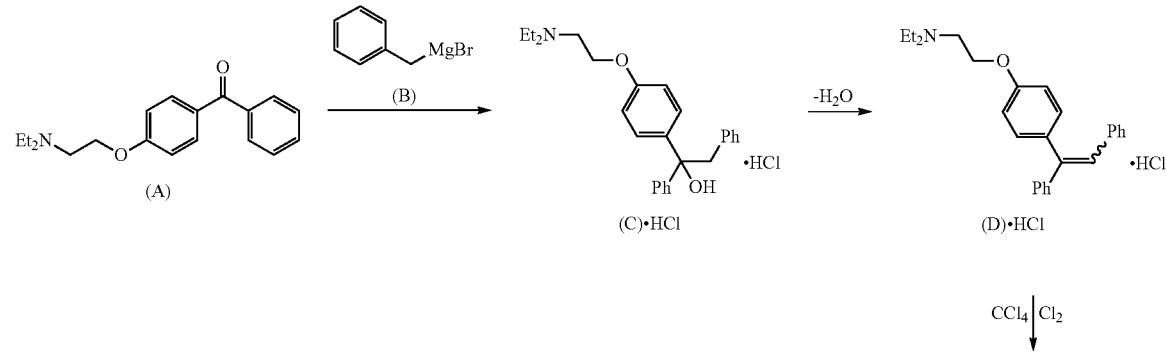

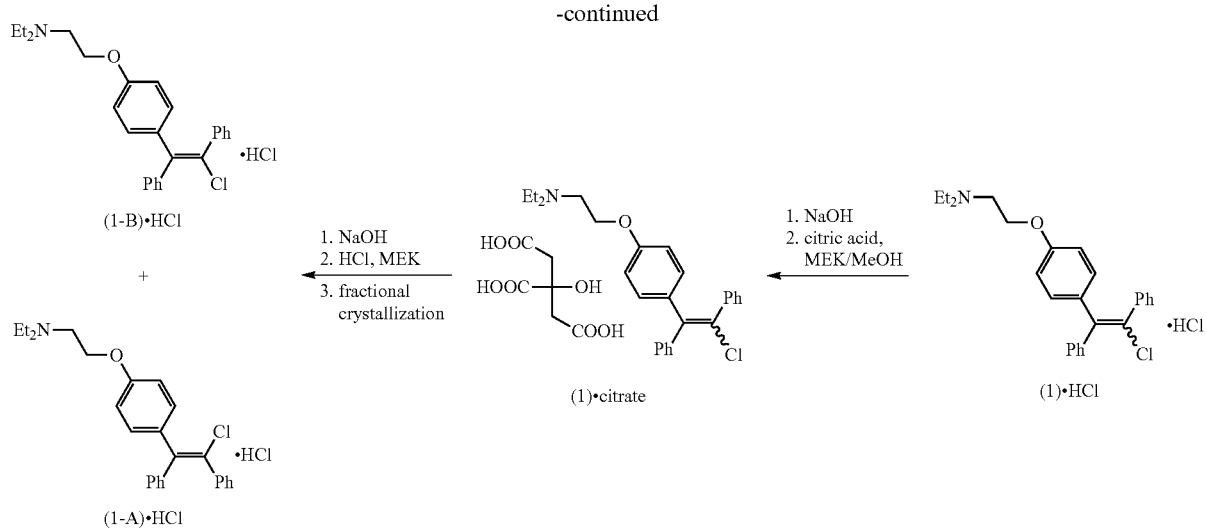

A number of other procedures reported for the preparation of clomiphene, including those described in U.S. Pat. No. 2,914,563 A, WO 2014/031177 A1, U.S. Pat. No. 9,428,442 B2, and U.S. Pat. No. 9,914,696 B2, follow the same basic synthetic approach comprising Grignard addition of benzylmagnesium bromide to substituted diaryl ketone (A), followed by dehydration and chlorination of the corresponding alcohol (C).

The major drawback of applying this synthetic approach to the preparation of zuclomiphene is that the resulting clomiphene that is provided is an isomeric mixture that is typically enriched in the E-isomer enclomiphene. According to U.S. Pat. No. 9,428,442 B2 for example, clomiphene afforded by treatment of triarylethylene (D) hydrochloride with N-chlorosuccinimide as chlorinating agent comprises only 30 to 50% of the Z-isomer zuclomiphene.

A second synthetic method for the preparation of clomiphene is described in Crenshaw et al. *J. Org. Chem.*, 1983, 48 (16), 2782-4. In this process, which is exemplified in Scheme 2, chlorobenzylphosphonate (E) is lithiated and subsequently reacted with aminoethoxy-substituted diphenyl ketone (A) in a Horner-Emmons-type manner to directly afford a clomiphene mixture (1) comprising 47% zuclomiphene and 53% enclomiphene. As above, this method provides clomiphene enriched in the undesired isomer.

Scheme 2 (Prior Art)

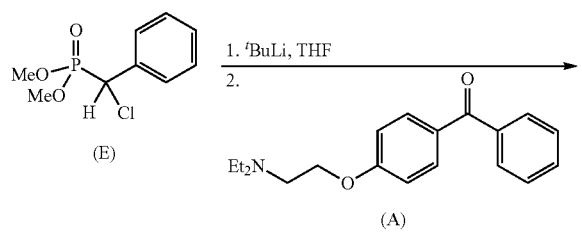

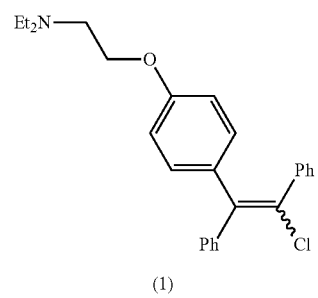

In A-hassan et al. *Synth. Commun.*, 1987, 17 (15), 1787-1796, clomiphene is prepared via a third method comprising hydroalumination of diphenylacetylene (F) followed by palladium-catalyzed cross-coupling as shown in Scheme 3. In this method, diphenylacetylene (F) undergoes hydroalumination to afford vinylalane (G) which is used as is or is cleaved with iodine to afford vinyl iodide (H). Subsequent cross-coupling of either vinylalane (G) with p-bromoanisole or of vinyl iodide (H) with (p-methoxyphenyl)zinc chloride affords methoxyaryl compound (1). Demethylation of (I) with sodium ethylthiolate followed by alkylation of the resulting phenoxide with 2-(N,N-diethylamino)ethyl chloride affords triarylethylene (D) which is chlorinated by treatment with N-chlorosuccinimide to afford clomiphene (1). The final step of this process comprises an analogous chlorination of triarylethylene (D) that is used in Palopoli et al. As such, this method also suffers from the same lack of stereo control mentioned above.

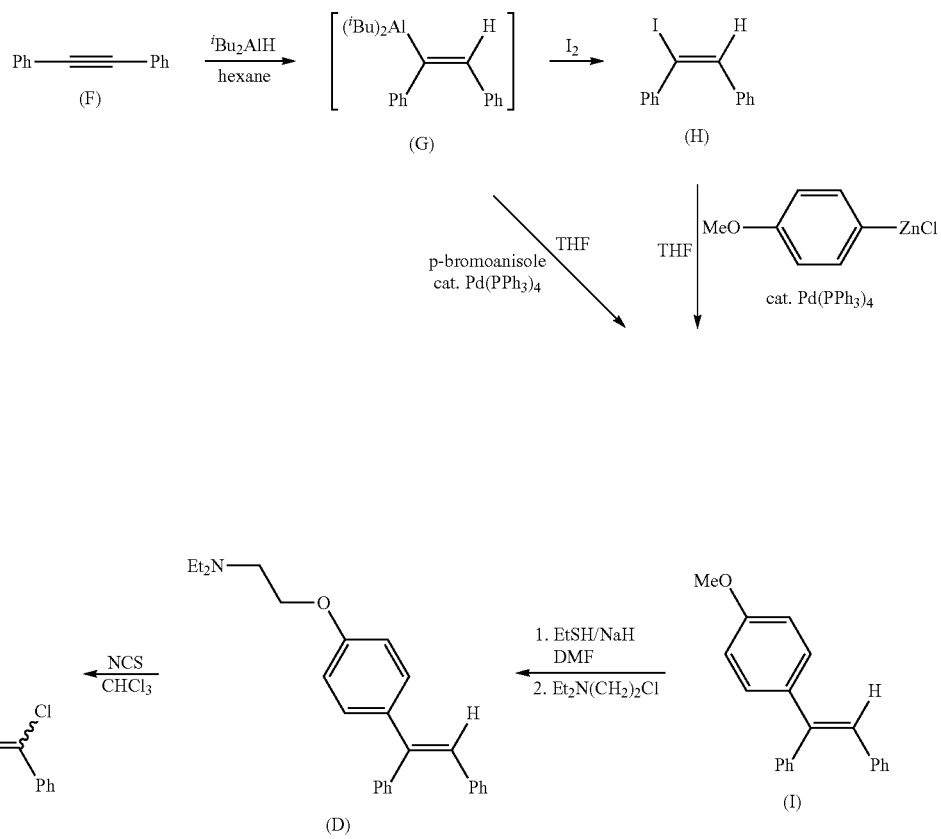

Retrieving pure zuclomiphene from an isomeric mixture that is obtained from the reported methods can be accomplished by fractional crystallization of zuclomiphene free form or a salt thereof as described in, for example, U.S. Pat. No. 3,848,030 A, Dolginova et al. *Pharm. Chem. J.* 1984, 11, 758-764 and Palopoli et al. *J. Med. Chem.* 1967, 10 (1), 84-6. The maximum recovery of zuclomiphene by fractional crystallization is limited by the isomeric composition of clomiphene established by the reported synthetic methods, which is generally balanced in favour of the undesirable enclomiphene isomer. As a result, the overall yield of known methods for the preparation of zuclomiphene is low.

Owing to the drawbacks of the existing processes, there remains a need for improved processes for the preparation of zuclomiphene (1-A), and the intermediates used in such preparations, that are more amenable to scale-up and use on a commercial scale.

SUMMARY OF THE INVENTION

The present invention provides improved processes for the preparation of zuclomiphene (1-A), or a salt thereof, as well as new intermediates and processes for the preparation thereof, as depicted in Scheme 4.

As shown in Scheme 4, in the processes of the present invention, zuclomiphene (1-A), or a salt thereof, may be prepared by a nickel-catalyzed carbometallation of diphenylacetylene (4) with the compound of Formula (3), followed by chlorination. The processes of the invention provide either zuclomiphene (1-A), or the intermediate of Formula (2-A), which can be further reacted to convert moiety G to the desired (N,N-diethylamino)ethoxy group of zuclomiphene (1-A).

Scheme 4

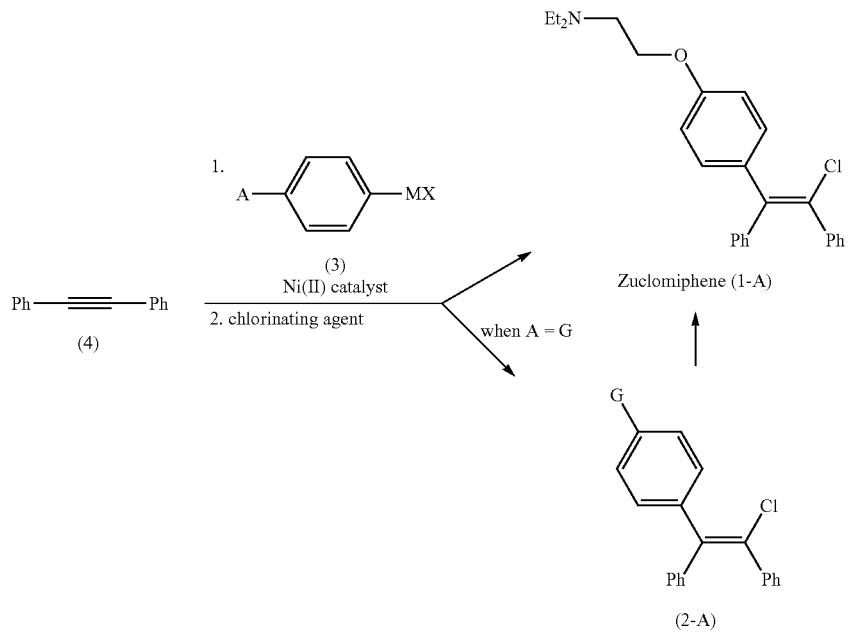

wherein
A is —OCH$_2$CH$_2$NEt$_2$ or G;
G is OPG or X$^1$;
PG is an alcohol protecting group;
M is zinc or magnesium; and
X and X$^1$ are independent halide groups.

Embodiments of the present invention are stereoselective and provide zuclomiphene (1-A) having high isomeric purity in good overall yield thereby providing important advantages that are applicable to the commercial preparation of zuclomiphene (1-A). Furthermore, the processes of the present invention start from readily available diphenylacetylene and are practical and industrially applicable.

Accordingly, in a first aspect of the present invention, there is provided a process for the preparation of zuclomiphene (1-A):

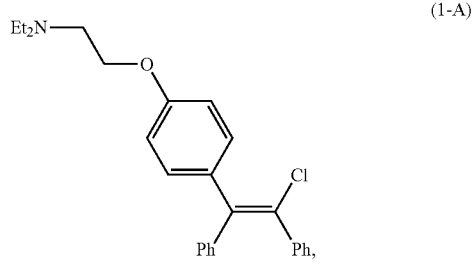

or a salt thereof, comprising:
(i) reacting diphenylacetylene, in the presence of a nickel (II) catalyst, with a compound of Formula (3):

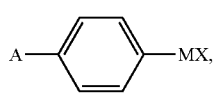

followed by a chlorinating agent,
wherein
A is —OCH$_2$CH$_2$NEt$_2$ or G;
M is zinc or magnesium; and
X is halide;
to provide either zuclomiphene (1-A) when A is —OCH$_2$CH$_2$NEt$_2$ or, when A is G, a compound of Formula (2-A):

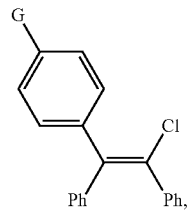

wherein
G is OPG or X$^1$;
PG is an alcohol protecting group;
X$^1$ is halide; and
(ii) when A is G, converting the G group in the compound of Formula (2-A) to the —OCH$_2$CH$_2$NEt$_2$ group of zuclomiphene (1-A).

In a preferred embodiment of the first aspect, M is magnesium and X is chloride or bromide.

In another preferred embodiment of the first aspect, the chlorinating agent is selected from the group consisting of chlorine, N-chlorosuccinimide, thionyl chloride, phosphorus trichloride, phosphorus pentachloride, phosphorus oxychloride, hexachloroethane and 1,3-dichloro-5,5-dimethylhydantoin. Preferably, the chlorinating agent is 1,3-dichloro-5,5-dimethylhydantoin.

In another preferred embodiment of the first aspect, the nickel(II) catalyst is selected from the group consisting of nickel(II) chloride, nickel(II) chloride hexahydrate, nickel (II) bromide, nickel(II) chloride ethylene glycol dimethyl ether complex, nickel(II) bromide ethylene glycol dimethyl ether complex, nickel(II) acetylacetonate, and nickel(II) acetate tetrahydrate. Preferably, the nickel(II) catalyst is nickel(II) chloride hexahydrate.

In another preferred embodiment of the first aspect, the reaction of diphenylacetylene and the compound of Formula (3) is conducted in the presence of a solvent (S1) selected from the group consisting of aromatic hydrocarbons, ethers, and mixtures thereof.

In further preferred embodiment of the first aspect, the reaction of diphenylacetylene and the compound of Formula (3) is conducted at a temperature in the range of about 50° C. to about 70° C.

In a further preferred embodiment of the first aspect, the compound of Formula (2-A) is a compound of Formula (2-A1):

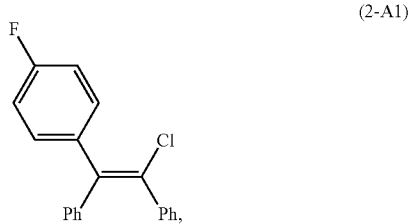

(2-A1)

and the process of converting the compound of Formula (2-A) to zuclomiphene (1-A), or a salt thereof, comprises reacting the compound of Formula (2-A1) with Et$_2$NCH$_2$CH$_2$OH.

Within this preferred embodiment of the first aspect, the reaction of the compound of Formula (2-A1) with Et$_2$NCH$_2$CH$_2$OH is conducted in the presence of a base (B1) and a solvent (S3). Preferably, the base (B1) is selected from the group consisting of potassium tert-butoxide, sodium tert-butoxide, sodium hydride, and potassium hydride. Preferably, the solvent (S3) is an ether. Further preferred within this embodiment is that the solvent (S3) is selected from the group consisting of tetrahydrofuran, 2-methyltetrahydrofuran, and 1,4-dioxane and the base (B1) is potassium tert-butoxide.

In a further preferred embodiment of the first aspect, the compound of Formula (2-A) is a compound of Formula (2-A3):

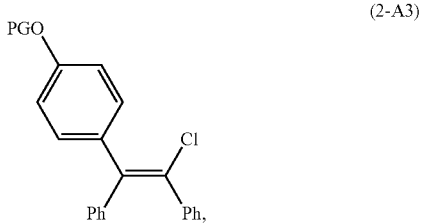

(2-A3)

wherein
PG is an alcohol protecting group,
and the process of converting the compound of Formula (2-A) to zuclomiphene (1-A), or a salt thereof, comprises deprotecting the compound of Formula (2-A3) and alkylating the resulting intermediate with a compound of Formula Et$_2$NCH$_2$CH$_2$LG, or a salt thereof, wherein LG is a leaving group.

Within this preferred embodiment of the first aspect, PG is preferably selected from the group consisting of an unsubstituted alkyl group having 1 to 6 carbon atoms, an alkyl ether group having 2 to 6 carbon atoms, a substituted or unsubstituted arylalkyl group having 1 to 3 carbon atoms in the alkyl portion and 6 to 14 ring carbon atoms in the aryl portion, and a SiR'R"R''' group wherein R', and R", R''' are independently selected from the group consisting of an alkyl group having 1 to 4 carbon atoms and a phenyl group. More preferably, PG is selected from the group consisting of methyl, ethyl, n-propyl, isopropyl, n-butyl, sec-butyl, tert-butyl, methoxymethyl, methoxyethoxymethyl, 2-tetrahydropyranyl, benzyl, p-methoxybenzyl, trimethylsilyl, t-butyldimethylsilyl, and triisopropylsilyl. Even more preferably, PG is selected from the group consisting of methyl, ethyl, n-propyl, isopropyl, n-butyl, sec-butyl and tert-butyl. Most preferably, PG is methyl.

Further preferred within this embodiment is that the deprotecting is conducted in the presence of an acid (A1). Preferably, the acid (A1) is a Lewis acid. Most preferably, the Lewis acid is boron tribromide.

Preferably, in this embodiment of the first aspect, the deprotecting is conducted in the presence of a solvent (S5) selected from the group consisting of halogenated hydrocarbons and ethers.

Within this embodiment, the deprotecting is preferably conducted at a temperature in the range of about −80° C. to about −40° C.

Further preferred within this embodiment is that LG is selected from the group consisting of halide and a sulfonate. Preferably, LG is chloride.

Within this embodiment of the first aspect, the alkylating reaction is preferably conducted in the presence of a solvent (S6) selected from the group consisting of acetone, N,N-dimethylformamide, and ethanol and a base (B3) selected from the group consisting of potassium carbonate, cesium carbonate, sodium carbonate, potassium hydroxide, and sodium hydroxide.

Preferably, in this embodiment of the first aspect, the alkylating reaction is conducted at a temperature in the range of about 40° C. and about 80° C.

In a further preferred embodiment of the first aspect, the compound of Formula (2-A) is a compound of Formula (2-A2):

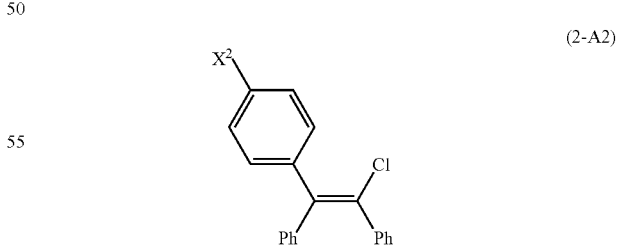

(2-A2)

wherein
X$^2$ is chloride, bromide or iodide,
and the process of converting the compound of Formula (2-A) to zuclomiphene (1-A), or a salt thereof, comprises reacting the compound of Formula (2-A2) with Et$_2$NCH$_2$CH$_2$OH in the presence of a copper catalyst and a base (B2).

Preferably, in this embodiment of the first aspect, $X^2$ is iodide and the copper catalyst is copper(I) iodide.

Further preferred within this embodiment is that the base (B2) is selected from the group consisting of tertiary amines, metal carbonates, and metal bicarbonates.

In a further preferred of the first aspect, the isomeric purity of zuclomiphene (1-A), or a salt thereof, that is produced is at least about 80%.

In another preferred embodiment of the first aspect, the zuclomiphene (1-A) that is produced is further converted to zuclomiphene (1-A) citrate.

In a second aspect of the present invention, there is provided a compound of Formula (2-A):

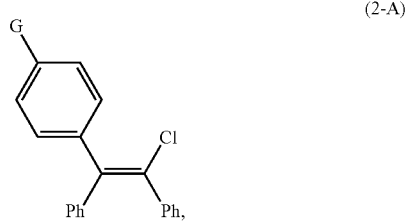

(2-A)

wherein
G is OPG or $X^1$;
PG is an alcohol protecting group selected from the group consisting of an unsubstituted alkyl group having 2 to 6 carbon atoms, an alkyl ether group having 2 to 6 carbon atoms, a substituted or unsubstituted arylalkyl group having 1 to 3 carbon atoms in the alkyl portion and 6 to 14 ring carbon atoms in the aryl portion, and a SiR'R"R''' group wherein R', and R", R' are independently selected from the group consisting of an alkyl group having 1 to 4 carbon atoms and a phenyl group; and $X^1$ is halide.

In a preferred embodiment of the second aspect, $X^1$ is selected from the group consisting of fluoride, chloride, bromide, iodide, and PG is selected from the group consisting of ethyl, n-propyl, isopropyl, n-butyl, sec-butyl, tert-butyl, methoxymethyl, methoxyethoxymethyl, 2-tetrahydropyranyl, benzyl, p-methoxybenzyl, trimethylsilyl, t-butyldimethylsilyl, and triisopropylsilyl. Preferably, G is fluoride.

DETAILED DESCRIPTION

The processes of the present invention provide zuclomiphene (1-A) stereoselectively from readily available materials in a concise, practical and industrially applicable manner.

As used herein, the term "alkyl", alone or as part of another substituent, means, unless otherwise stated, a straight chain, branched chain, or non-aromatic cyclic hydrocarbon radical having the number of carbon atoms designated. When there is no indication of the number of carbon atoms in the alkyl, it is meant, unless otherwise indicated by context, that there are from 1 to 6 carbon atoms. Examples of preferred alkyl groups include methyl, ethyl, n-propyl, iso-propyl, n-butyl, t-butyl, iso-butyl, and sec-butyl.

As used herein, the term "aryl", alone or as part of another substituent, means a polyunsaturated, aromatic, hydrocarbon radical which can comprise one, two or three rings which are fused together or linked covalently, having the number of ring carbon atoms designated. When there is no indication of the number of carbon atoms in the aryl, it is meant, unless otherwise indicated by context, that there are from 6 to 14 carbon atoms. Examples of preferred aryl groups include phenyl, 4-biphenyl, 9-fluorenyl, 1-naphthyl, 2-naphthyl, 2-anthryl, and 9-anthryl. A preferred aryl group is phenyl.

As used herein, the term "arylalkyl", alone or as part of another substituent, means, unless otherwise stated, an aryl substituent as defined herein attached through an alkyl radical to the parent structure. When there is no indication of the number of carbon atoms in the arylalkyl group, it is meant, unless otherwise indicated by context, that there are from 6 to 14 ring carbon atoms and 1 to 3 carbon atoms in the alkyl portion. Preferred examples of arylalkyl groups include benzyl and phenethyl.

As used herein, the term "substituted" refers to the replacement of one or more hydrogen atoms with a substituent selected from the group consisting of: alkyl, OR, halogen and $CF_3$. A substituted group may be mono-substituted or polysubstituted. As used herein, each R may be an alkyl group. Preferred examples of substituent groups on substituted aryl groups include methoxy, methyl, fluoride, and chloride.

As used herein, the term "alkyl ether", alone or as part of another substituent, means an alkyl chain bonded to another alkyl or substituted alkyl chain via an oxygen atom wherein alkyl is as defined herein having the number of carbon atoms designated. When there is no indication of the number of carbon atoms in the alkyl ether group, it is meant, unless otherwise indicated by context, that there are from 2 to 6 carbon atoms. Examples of preferred alkyl ether groups include methoxymethyl, methoxyethoxymethyl, and 2-tetrahydropyranyl.

As used herein, the term "isomeric purity" refers to the amount of the subject zuclomiphene (or a salt thereof) relative to the total amount of enclomiphene and zuclomiphene (or a salt thereof), expressed as a mole percentage.

As used herein, the term "citrate" refers to the dihydrogen citrate ion that is the counterion in zuclomiphene citrate.

As used herein, "room temperature" generally refers to a temperature of 20-25° C.

As used herein, the term "about" means "close to", and that variation from the exact value that follows the term is within amounts that a person of skill in the art would understand to be reasonable. For example, when the term "about" is used with respect to temperature, a variation of ±5° C. is generally acceptable when carrying out the processes of the present invention. When used with respect to mole equivalents, a variation of ±0.1 moles is generally acceptable.

In one embodiment of the present invention, zuclomiphene (1-A), or a salt thereof, and intermediates useful in the preparation thereof may be prepared by the process as set out in Scheme 4. Exemplary reagents and conditions for these processes are described herein.

In the processes and compounds of the invention, A is —$OCH_2CH_2NEt_2$ or G, wherein G is OPG or $X^1$, PG is an alcohol protecting group, and $X^1$ is halide.

In the processes and compounds of the invention, PG is an alcohol protecting group. Preferably, PG is a protecting group that is removable in neutral or acidic pH conditions. Preferably, PG is selected from the group consisting of an unsubstituted alkyl group having 1 to 6 carbon atoms, an alkyl ether group having 2 to 6 carbon atoms, a substituted or unsubstituted arylalkyl group having 1 to 3 carbon atoms in the alkyl portion and 6 to 14 ring carbon atoms in the aryl portion, and a SiR'R"R''' group wherein R', and R", R''' are independently selected from the group consisting of an alkyl group having 1 to 4 carbon atoms and a phenyl group. Preferably, PG is selected from the group consisting of methyl, ethyl, n-propyl, isopropyl, n-butyl, sec-butyl, tert-butyl, methoxymethyl, methoxyethoxymethyl, 2-tetrahydropyranyl, benzyl, p-methoxybenzyl, trimethylsilyl, t-butyldimethylsilyl, and triisopropylsilyl. More preferably, PG is selected from the group consisting of methyl, methoxymethyl, 2-tetrahydropyranyl, benzyl, p-methoxybenzyl, and t-butyldimethylsilyl. Most preferably, PG is methyl.

In the processes and compounds of the invention, $X^1$ is halide, preferably selected from the group consisting of fluoride, bromide, and iodide, and is most preferably fluoride.

In one embodiment of the present invention, there is provided a process for the preparation of zuclomiphene (1-A):

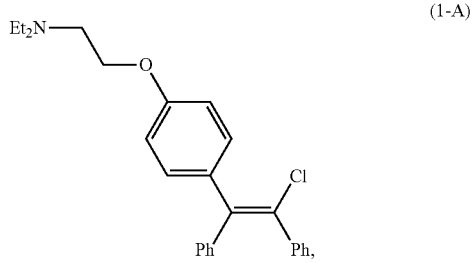

or a salt thereof, comprising:
(i) reacting diphenylacetylene, in the presence of a nickel (II) catalyst, with a compound of Formula (3):

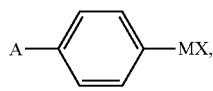

followed by a chlorinating agent,
wherein
A is —OCH$_2$CH$_2$NEt$_2$ or G;
M is zinc or magnesium; and
X is halide;
to provide either zuclomiphene (1-A) when A is —OCH$_2$CH$_2$NEt$_2$ or, when A is G, a compound of Formula (2-A):

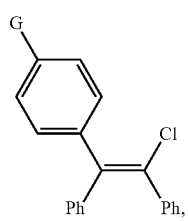

wherein
G is OPG or $X^1$;
PG is an alcohol protecting group;
$X^1$ is halide; and
(ii) when A is G, converting the G group in the compound of Formula (2-A) to the —OCH$_2$CH$_2$NEt$_2$ group of zuclomiphene (1-A).

M is zinc or magnesium, preferably magnesium. X is halide, preferably selected from the group consisting of chloride and bromide. Most preferably, MX is magnesium chloride. In an embodiment, the magnesium chloride Grignard is preferred in order to avoid formation of brominated impurity (IMP) in the reaction, detectable by HPLC, which can occur with the use of the magnesium bromide Grignard.

The nickel(II) catalyst may be selected from the group consisting of nickel(II) chloride (NiCl$_2$), nickel(II) chloride hexahydrate (NiCl$_2$.6H$_2$O), nickel(II) bromide (NiBr$_2$), nickel(II) chloride ethylene glycol dimethyl ether complex ([NiCl$_2$(dme)]), nickel(II) bromide ethylene glycol dimethyl ether complex ([NiBr$_2$(dme)]), nickel(II) acetylacetonate (Ni(acac)$_2$), and nickel(II) acetate tetrahydrate (Ni(OAc)$_2$.4H$_2$O). Most preferably, the nickel(II) catalyst is nickel(II) chloride (NiCl$_2$) or nickel(II) chloride hexahydrate (NiCl$_2$.6H$_2$O). The amount of nickel(II) catalyst may be in the range of about 0.1 mol % to about 5 mol %, preferably it is in the range of about 1 mol % and about 3 mol %, with respect to the amount of diphenylacetylene.

The reaction of diphenylacetylene and the compound of Formula (3) may be conducted in the presence of a solvent (S1). Solvent (S1) is preferably selected from the group consisting of halogenated hydrocarbons, aromatic hydrocarbons, ethers, and mixtures thereof. More preferably, solvent (S1) is selected from the group consisting of methyl t-butyl ether, tetrahydrofuran, 2-methyltetrahydrofuran, 1,4-dioxane, toluene, and mixtures thereof. Most preferably, solvent (S1) is toluene.

The reaction of diphenylacetylene and the compound of Formula (3) may be conducted at any suitable temperature, and is preferably conducted at a temperature in the range of about 20° C. to the boiling point of the reaction mixture. Preferably, the suitable temperature is in the range of about 50° C. to about 80° C.

The reaction of diphenylacetylene and the compound of Formula (3) is thought to generate an intermediate alkenyl-metal halide species of Formula (2-int):

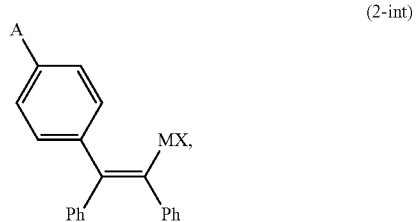

wherein
A is —OCH$_2$CH$_2$NEt$_2$ or G;
M is zinc or magnesium;
G is OPG or $X^1$;
PG is an alcohol protecting group; and
X and $X^1$ are independent halide groups,
which undergoes reaction with a chlorinating agent, to afford either zuclomiphene (1-A), or a salt thereof, or the compound of Formula (2-A).

The chlorinating agent may be selected from the group consisting of chlorine (Cl$_2$), N-chlorosuccinimide (NCS), thionyl chloride (SOCl$_2$), phosphorus trichloride (PCl$_3$), phosphorus pentachloride (PCl$_5$), phosphorus oxychloride (POCl$_3$), hexachloroethane, and 1,3-dichloro-5,5-dimethylhydantoin. Preferably, the chlorinating agent is 1,3-dichloro-5,5-dimethylhydantoin.

The chlorinating agent may be used as is or it may be dissolved in a solvent (S2). The solvent (S2) may be the same or different from the solvent (S1) but is preferably selected from the same group of solvents including halogenated hydrocarbons, aromatic hydrocarbons, ethers, and mixtures thereof. Preferably, solvent (S2) is toluene.

The chlorination reaction may be conducted at any suitable temperature, and is preferably conducted at a temperature in the range of about 0° C. to about 50° C., more preferably the suitable temperature is in the range of about 20° C. to about 30° C.

Compounds of Formula (3) wherein M is magnesium and X is halide are commercially available. Alternatively, a compound of Formula (3) may be prepared by any desired method including, for example, by reacting the corresponding p-substituted phenyl halide with magnesium or zinc or by lithium-halide exchange of the corresponding p-substituted phenyl halide followed by transmetallation with magnesium halide or zinc halide. Preferably, when M is magnesium and X is chloride, the compound of Formula (3) is prepared by treating 4-fluorophenyl iodide with an alkylmagnesium chloride, preferably isopropylmagnesium chloride. The corresponding alkyl iodide by-product can be removed by, for example, distillation, prior to the reaction with diphenylacetylene.

Step (ii) is conducted when A in the compound of Formula (3) is G, corresponding with a compound of Formula (3-A):

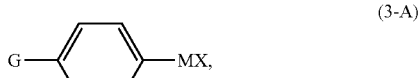

(3-A)

and the product of step (i) is a compound of Formula (2-A):

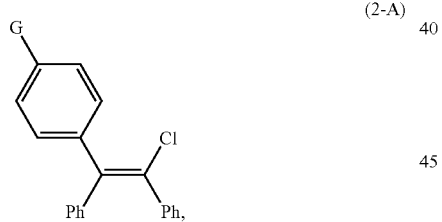

(2-A)

wherein
G is OPG or $X^1$;
PG is an alcohol protecting group; and
$X^1$ is halide.

In an embodiment of step (ii), G is fluoride and the compound of Formula (2-A) is a compound of Formula (2-A1):

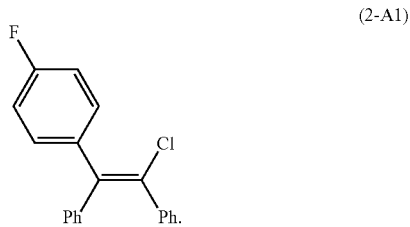 [SMILES: Fc1ccc(/C(=C(\Cl)c2ccccc2)c2ccccc2)cc1]

(2-A1)

In this embodiment, the process of converting the compound of Formula (2-A) to zuclomiphene (1-A), or a salt thereof, comprises reacting the compound of Formula (2-A1) with $Et_2NCH_2CH_2OH$ (ie. 2-(N,N-diethylamino)ethanol) in the presence of a base (B1) and a solvent (S3).

The reaction of the compound of Formula (2-A1) with $Et_2NCH_2CH_2OH$ is conducted in the presence of a base (B1). The base (B1) may be any suitable base capable of facilitating an $S_NAr$-type displacement. Preferably, the base (B1) is selected from the group consisting of metal alkoxides and metal hydrides. More preferably, the base (B1) is selected from the group consisting of potassium tert-butoxide, sodium tert-butoxide, sodium hydride, and potassium hydride. Most preferably the base (B1) is potassium tert-butoxide.

The reaction of the compound of Formula (2-A1) with $Et_2NCH_2CH_2OH$ is conducted in the presence of a solvent (S3). Preferably, the solvent (S3) is selected from the group consisting of ethers, sulfoxides, and amides. More preferably, the solvent (S3) is selected from the group consisting of dimethyl sulfoxide, N,N-dimethylformamide, tetrahydrofuran, 2-methyltetrahydrofuran, and 1,4-dioxane. Most preferably, the solvent (S3) is 1,4-dioxane.

The reaction of the compound of Formula (2-A1) with $Et_2NCH_2CH_2OH$ may be conducted at any suitable temperature, and is preferably conducted at or near the boiling point of the reaction mixture. Most preferably, the suitable temperature is in the range of about 70° C. to about 110° C.

In another embodiment of step (ii), G is chloride, bromide, or iodide and the compound of Formula (2-A) is a compound of Formula (2-A2):

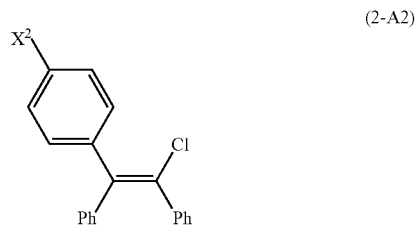

(2-A2)

wherein $X^2$ is chloride, bromide or iodide. In this embodiment, the process of converting the compound of Formula (2-A) to zuclomiphene (1-A), or a salt thereof, comprises reacting the compound of Formula (2-A2) with $Et_2NCH_2CH_2OH$ in the presence of a copper catalyst and a base (B2).

The reaction of the compound of Formula (2-A2) with $Et_2NCH_2CH_2OH$ is conducted in the presence of a copper catalyst, preferably selected from the group consisting of copper(I) chloride, copper(I) bromide, copper(I) iodide, copper(I) oxide, copper(I) acetate, copper(I) thiocyanate, and copper(I) sulfide, and is most preferably copper(I) iodide. Preferably, the amount of copper catalyst relative to the amount of the compound of Formula (2-A2) is between about 1 mol % and about 30 mol %, and is most preferably between about 10 mol % and about 25 mol %.

In the reaction of the compound of Formula (2-A2) with $Et_2NCH_2CH_2OH$, an excess amount of $Et_2NCH_2CH_2OH$ can also function as a base. Alternatively, the reaction may be conducted in the presence of a base (B2) that is preferably selected from the group consisting of tertiary amines, metal carbonates, and metal bicarbonates. Preferably, base (B2) is selected from the group consisting of sodium carbonate, sodium bicarbonate, potassium carbonate, potassium bicarbonate, lithium carbonate, triethylamine, and diisopropylethylamine. Most preferably, base (B2) is selected from the group consisting of triethylamine, potassium carbonate, and mixtures thereof.

The reaction of the compound of Formula (2-A2) with $Et_2NCH_2CH_2OH$ may be conducted in the presence of a solvent (S4), preferably a high-boiling solvent selected from the group consisting of ethers, aromatic hydrocarbons, amides, and nitriles. More preferably, the solvent (S4) is selected from the group consisting of 1,4-dioxane, toluene, N,N-dimethylformamide, and acetonitrile.

The reaction of the compound of Formula (2-A2) with $Et_2NCH_2CH_2OH$ may be conducted at any suitable temperature, and is preferably conducted at or near the boiling point of the reaction mixture. Most preferably, the suitable temperature is in the range of about 80° C. to about 130° C.

In another embodiment of step (ii), G is OPG and the compound of Formula (2-A) is a compound of Formula (2-A3):

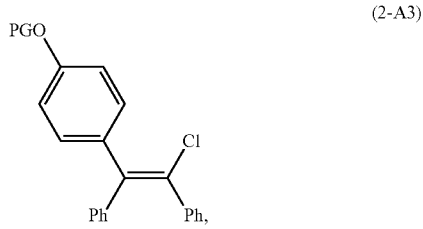

(2-A3)

wherein PG is an alcohol protecting group. In this embodiment, the process of converting the compound of Formula (2-A) to zuclomiphene (1-A), or a salt thereof, comprises deprotecting the compound of Formula (2-A3) and alkylating the resulting intermediate with a compound of Formula $Et_2NCH_2CH_2LG$, or a salt thereof, wherein LG is a leaving group.

Preferably, PG in the compound of Formula (2-A3) is a protecting group that is removable in neutral or acidic pH conditions in order to avoid any isomerization of the double bond that may occur as a result of exposure to basic pH conditions. Preferably, PG is a protecting group that is removable by treatment with tetrabutylammonium fluoride (TBAF) or an acid (A1), which may be any suitable Lewis or Brønsted acid. Preferably, acid (A1) is selected from the group consisting of boron tribromide ($BBr_3$), trimethylsilyl iodide (TMSI), trimethylsilyl chloride (TMSCl), aluminum chloride ($AlCl_3$), tin (IV) chloride ($SnCl_4$), titanium tetrachloride ($TiCl_4$) and hydrochloric acid. Most preferably, acid (A1) is boron tribromide ($BBr_3$).

The deprotection of the compound of Formula (2-A3) may be conducted in the presence of a solvent (S5), preferably selected from the group consisting of halogenated hydrocarbons and ethers. More preferably, the solvent (S5) is selected from the group consisting of dichloromethane and methyl t-butyl ether. Most preferably, the solvent (S5) is dichloromethane.

The deprotection of the compound of Formula (2-A3) may be conducted at any suitable temperature, and is preferably conducted at sub-zero temperatures. More preferably, the suitable temperature is between about −80° C. and about 0° C. Most preferably, the suitable temperature is between about −80° C. and about −40° C.

In an embodiment, the product of deprotecting the compound of Formula (2-A3) is a compound of Formula (1-int):

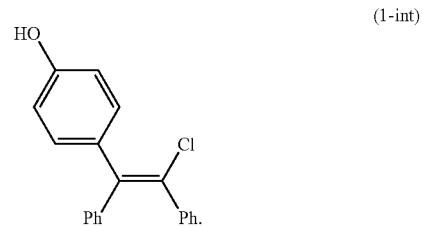 [SMILES: Oc1ccc(/C(=C(\Cl)c2ccccc2)c2ccccc2)cc1]

(1-int)

Intermediate (1-int) may be isolated in the processes of the present invention or it may be used in situ without isolation.

In the alkylation reaction, LG in the compound of Formula $Et_2NCH_2CH_2LG$ is a leaving group, preferably selected from the group consisting of halide and a sulfonate. Preferred sulfonates are selected from methanesulfonate, toluenesulfonate, and trifluoromethanesulfonate. Preferably, LG is halide selected from the group consisting of chloride, bromide, and iodide, and is most preferably chloride. Preferably, the compound of Formula $Et_2NCH_2CH_2LG$ is provided as a salt such as a hydrochloride salt, which is neutralised for the reaction. Neutralisation of a salt of $Et_2NCH_2CH_2LG$ may lead to formation of the corresponding aziridinium ion of this compound, which may be the active species in the reaction.

The alkylation reaction is preferably conducted in the presence of a base (B3). Base (B3) is preferably selected from the group consisting of metal carbonates, metal bicarbonates, and metal hydroxides. Preferably, base (B3) is selected from the group consisting of potassium carbonate, cesium carbonate, sodium carbonate, potassium hydroxide, and sodium hydroxide. Most preferably, the base (B3) is cesium carbonate.

The alkylation reaction may be conducted using phase-transfer conditions to avoid prolonged contact of the compound of Formula (1-int) to strong basic conditions such as when using sodium hydroxide. A suitable phase-transfer catalyst is selected from the group consisting of tetrabutylammonium bromide, benzyltriethylammonium chloride, and methyltributylammonium chloride. Preferably, the phase transfer catalyst is benzyltriethylammonium chloride.

The alkylation reaction may be conducted in the presence of a solvent (S6), preferably selected from the group consisting of ketones, amides and alcohols. More preferably, the solvent (S6) is selected from the group consisting of acetone, N,N-dimethylformamide, and ethanol. Most preferably, the solvent (S6) is N,N-dimethylformamide The alkylation reaction may be conducted at any suitable temperature, and is preferably conducted at a temperature in the range of about 30° C. to the boiling point of the reaction mixture. More preferably, the temperature is in the range of about 40° C. and about 80° C.

Preferably, the reaction of diphenylacetylene with the compound of Formula (3) is stereoselective in favour of the Z-configuration. Preferably, the isomeric composition of zuclomiphene (1-A) or the compound of Formula (2-A) that is produced is enriched in the Z-isomer relative to the E-isomer. Preferably, the isomeric purity of the zuclomiphene (1-A) or the compound of Formula (2-A) that is produced is at least about 60%, more preferably the isomeric purity is at least about 80%. Even more preferably, the isomeric purity of the zuclomiphene (1-A) or the compound of Formula (2-A) that is produced is at least about 90%, most preferably, the isomeric purity is at least about 95%.

The zuclomiphene (1-A), or a salt thereof, that is provided may be subjected to further purification steps to increase the chemical and/or isomeric purity. Preferably, purification comprises crystallization of a salt of zuclomiphene (1-A) from a suitable solvent. A suitable salt is derived from an acid (HA) which may bear one or more acidic protons and is preferably selected from the group consisting of binaphthyl hydrogen phosphate, D,L-aspartic acid, cyclamic acid, fumaric acid, L-glutamic acid, hippuric acid, L-malic acid, malonic acid, nicotinic acid, di-p-toluoyl-D-tartaric acid, saccharin, D-tartaric acid, and citric acid. Preferably, the acid (HA) is binaphthyl hydrogen phosphate or citric acid and the molar ratio of zuclomiphene to acid (HA) is about 1:1.

In another embodiment of the present invention, there is provided a compound of Formula (2-A):

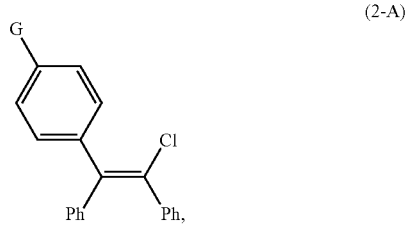

(2-A)

wherein G is OPG or X$^1$; PG is an alcohol protecting group selected from the group consisting of an unsubstituted alkyl group having 2 to 6 carbon atoms, an alkyl ether group having 2 to 6 carbon atoms, a substituted or unsubstituted arylalkyl group having 1 to 3 carbon atoms in the alkyl portion and 6 to 14 ring carbon atoms in the aryl portion, and a SiR'R''R''' group wherein R', and R'', R''' are independently selected from the group consisting of an alkyl group having 1 to 4 carbon atoms and a phenyl group; and X$^1$ is halide. Preferably, in the compound of Formula (2-A), X$^1$ is selected from the group consisting of fluoride, chloride, bromide, iodide, and PG is selected from the group consisting of ethyl, n-propyl, isopropyl, n-butyl, sec-butyl, tert-butyl, methoxymethyl, methoxyethoxymethyl, 2-tetrahydropyranyl, benzyl, p-methoxybenzyl, trimethylsilyl, t-butyldimethylsilyl, and triisopropylsilyl. More preferably, in the compound of Formula (2-A), G is fluoride.

EXAMPLES

The following examples are illustrative of some of the embodiments of the invention described herein. It will be apparent to the person skilled in the art that various alterations to the described processes in respect of the reactants, reagents and conditions may be made when using the processes of the present invention without departing from the scope or intent thereof.

Example 1: Preparation of (Z)-4-(2-Chloro-1,2-Diphenylethenyl) Fluorobenzene (Compound of Formula (2-A1))

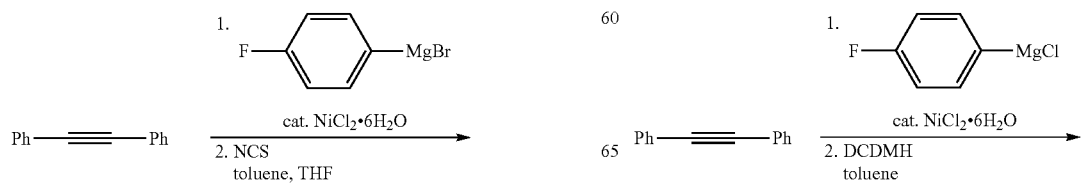

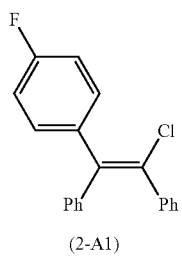

(2-A1)

A mixture of diphenylacetylene (1.00 g, 5.61 mmol) and nickel(II) chloride hexahydrate (0.0029 g, 0.021 mmol, 0.4 mol %) was purged with nitrogen gas three times prior to addition of toluene (15 mL), and a 1 M solution of 4-fluorophenylmagnesium bromide in tetrahydrofuran (6.7 mL, 6.7 mmol). The reaction mixture was then heated to 60° C. and maintained at this temperature until all of the diphenylacetylene was consumed. The reaction mixture was then cooled to room temperature and N-chlorosuccinimide (0.90 g, 6.73 mmol) was charged. Following a period of stirring at room temperature for two hours, the reaction mixture was charged into saturated aqueous ammonium chloride solution and extracted with methyl t-butyl ether. The organic phase was washed with dilute sodium hydroxide, water and brine prior to filtration through anhydrous sodium sulfate and evaporation to dryness in vacuo to afford crude compound of Formula (2-A1) as a yellow solid (1.67 g 97% yield).

The yellow solid (1.67 g) was subjected to further purification by suspending it in hot isopropanol (7 mL) and cooling to 0-5° C. prior to filtration and drying in vacuo to afford the compound of Formula (2-A1) as a yellow solid (1.25 g, 72% yield from diphenylacetylene). Estimated isomeric purity (Z-isomer, $^1$H NMR): about 95%.

$^1$H-NMR of the compound of Formula (2-A1): (CDCl$_3$, 300 MHz, ppm) δ 7.28-7.40 (m, 4H). 7.16-7.22 (m, 3H), 7.01-7.16 (m, 5H), 6.89-6.98 (m, 2H).

Example 1A: Preparation of (Z)-4-(2-chloro-1,2-diphenylethenyl) fluorobenzene (Compound of Formula (2-A1))

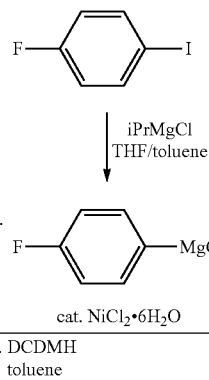

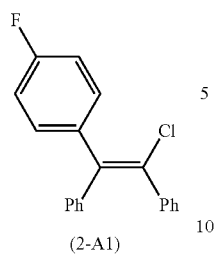

(2-A1)

Isopropyl magnesium chloride (2.0 M in THF, 98 mL, 196.4 mmol) was added to 1-fluoro-4-iodobenzene (43.60 g, 196.4 mmol) and the mixture was stirred at room temperature for 30 minutes. Toluene (125 mL) was charged to this mixture and the solution was distilled to afford a residue of the Grignard reagent. Diphenyl acetylene (25.00 g, 140.3 mmol) and nickel (II) chloride hexahydrate (0.67 g, 2.81 mmol) was dissolved in toluene (225 mL), purged with nitrogen gas three times and stirred at room temperature. The acetylene solution was charged to the Grignard residue at room temperature followed by a toluene wash (25 mL). The reaction was then heated to 70-75° C. until all the diphenylacetylene was consumed. A flask containing 1,3-dichloro-5,5-dimethyl-2,4-imidazolidinedione (69.09 g, 350.7 mmol) and toluene (125 mL) was heated to 50-55° C. To the flask containing 1,3-dichloro-5,5-dimethyl-2,4-imidazolidinedione was charged the Grignard solution. Following a period of stirring at 50-55° C. for 30 minutes, the reaction mixture was charged with 10% aqueous sodium thiosulfite. The organic phase was washed with 10% aqueous sodium thiosulfate and saturated ammonium chloride. The combined aqueous phases were extracted with toluene and the combined organic phases were dried over anhydrous sodium sulfate, filtered, and evaporated to dryness in vacuo to afford crude compound of Formula (2-A1) as a yellow solid (63.01 g) free of brominated impurity (IMP).

The yellow solid was subjected to further purification by suspending it in hot ethanol (150 mL) and cooling to 0-5° C. prior to filtration and drying in vacuo to afford the compound of Formula (2-A1) as a yellow solid (20.32 g, 47% yield) HPLC purity (83.4 a %). The yellow solid (20.00 g) was subjected to further purification by suspending it in hot ethanol (60 mL) and cooling to 0-5° C. prior to filtration and drying in vacuo to afford the compound of Formula (2-A1) as a yellow solid (15.22 g, 76% recovery) HPLC purity 95.98 a %.

Example 2: Preparation of (Z)-4-(2-chloro-1,2-diphenylethenyl) methoxybenzene (compound of Formula (2-A3'))

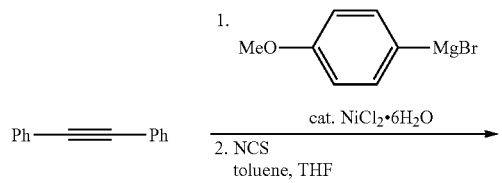

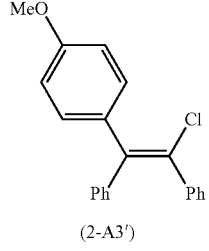

(2-A3')

4-Bromoanisole (0.84 mL, 6.73 mmol) was added over one hour to a suspension of magnesium turnings (0.18 g, 7.29 mmol) in tetrahydrofuran (6 mL) to afford a solution of 4-methoxyphenylmagnesium bromide. A dry flask containing a mixture of diphenylacetylene (1.00 g, 5.61 mmol) and nickel(II) chloride hexahydrate (0.0029 g, 0.021 mmol, 0.4 mol %) was purged with nitrogen gas three times prior to addition of toluene (15 mL), and the prepared 4-methoxyphenylmagnesium bromide solution (6.7 mL, 6.7 mmol). The reaction mixture was then heated to 60° C. and maintained at this temperature until all of the diphenylacetylene was consumed. The reaction mixture was then cooled to room temperature and N-chlorosuccinimide (0.90 g, 6.73 mmol) was charged. Following a period of stirring at room temperature for 1.5 hours, the reaction mixture was charged into saturated aqueous ammonium chloride solution and extracted with methyl t-butyl ether. The organic phase was washed with dilute sodium hydroxide, water and brine prior to filtration through anhydrous sodium sulfate and evaporation to dryness in vacuo to afford crude compound of Formula (2-A3') as a yellow solid (1.91 g).

The yellow solid (1.91 g) was subjected to further purification by suspending it in hot isopropanol (8 mL) and cooling to room temperature prior to filtration and drying in vacuo to afford the compound of Formula (2-A3') as a yellow solid (1.35 g, 75% yield from diphenylacetylene). Estimated isomeric purity (Z-isomer, $^1$H NMR): about 95%.

$^1$H-NMR of the compound of Formula (2-A3'): (CDCl$_3$, 300 MHz, ppm) δ 7.28-7.33 (m, 4H), 7.14-7.19 (m, 3H), 7.05-7.10 (m, 3H), 6.94-6.97 (m, 2H), 6.90 (app. d, J=8.6 Hz, 2H), 3.83 (s, 3H).

Example 3: Preparation of (Z)-4-(2-chloro-1,2-diphenylethenyl)phenol (compound of Formula (1-int))

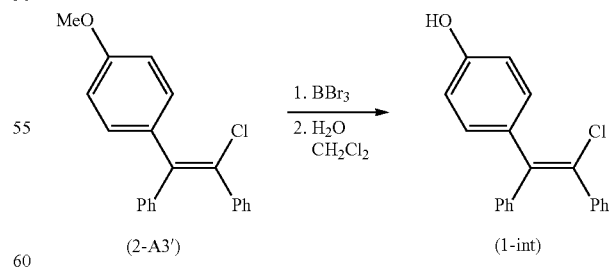

To a cooled (−80° C.) solution of the compound of Formula (2-A3') (1.00 g, 3.12 mmol) in dichloromethane (20 mL) was added a 1 M solution of boron tribromide in dichloromethane (9.5 mL, 9.55 mmol) while maintaining the internal temperature below −50° C. Cooling was discontinued and the reaction mixture was allowed to warm to room temperature. Following 21 hours, the reaction mixture was then charged into water, the phases were separated and the aqueous phase was extracted once with dichloromethane. The combined organic phase was washed with water and brine, filtered through anhydrous sodium sulfate and concentrated to dryness in vacuo to afford crude compound of Formula (1-int) as a grey solid (1.08 g).

$^1$H-NMR of the compound of Formula (1-int) (CDCl$_3$, 400 MHz, ppm): δ 7.28-7.30 (m, 4H, 7.13-7.18 (m, 3H), 7.04-7.09 (m, 3H), 6.93-6.97 (m, 2H), 6.82 (app. d, J=8.2 Hz).

Example 4: Preparation of Zuclomiphene (1-A) Citrate from the Compound of Formula (2-A1)

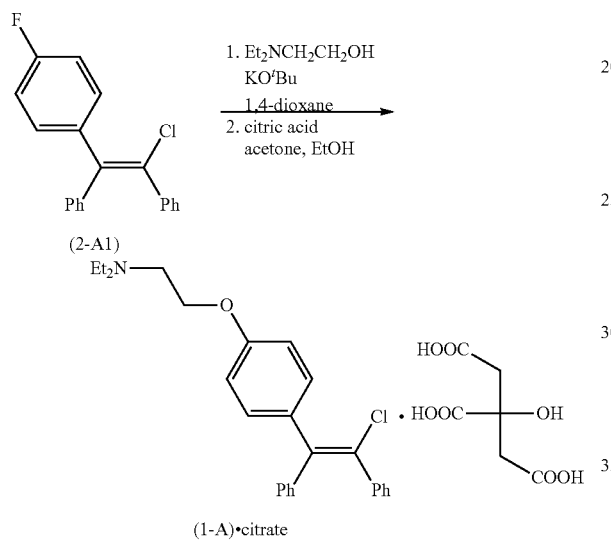

(1-A)·citrate

A solution of the compound of Formula (2-A1) (1.00 g, 3.24 mmol), as prepared in Example 1, in 1,4-dioxane (6 mL) was charged to a solution of potassium tert-butoxide (0.55 g, 4.86 mmol) and 2-(N,N-diethylamino)ethanol (0.7 mL, 5.18 mmol) in 1,4-dioxane (4 mL) at room temperature. The reaction mixture was heated to 100° C. for two hours after which it was cooled to room temperature and concentrated in vacuo to afford an oil. The oil was treated with methyl t-butyl ether and dilute hydrochloric acid. The phases were separated, and the organic phase was extracted once more with dilute hydrochloric acid. The pH of the combined aqueous phases was adjusted to 13-14 with sodium hydroxide prior to extraction with methyl t-butyl ether two times. The combined organic phases were filtered through anhydrous sodium sulfate and concentrated to dryness in vacuo to afford crude zuclomiphene (1-A) as a thick oil (0.76 g, 58% yield).

$^1$H-NMR of zuclomiphene (1-A) (CDCl$_3$, 400 MHz, ppm): δ 7.29-7.31 (m, 4H), 7.14-7.17 (m, 3H), 7.06-7.09 (m, 3H), 6.94-6.97 (m, 2H), 6.89 (app. d, J=8.9 Hz, 2H), 4.06 (t, J=6.4 Hz, 2H), 2.88 (t, J=6.4 Hz, 2H), 2.64 (q, J=7.1 Hz, 4H, 1.07 (t, J=7.1 Hz, 6H).

The oil (0.76 g, 1.87 mmol) was dissolved in acetone (5 mL) and a solution of citric acid (0.33 g, 1.68 mmol) in ethanol (0.4 mL) was added. A white solid precipitate formed within minutes and was filtered after one hour of stirring at room temperature. The filter cake was washed once with acetone, then dried in vacuo at room temperature to afford zuclomiphene (1-A) citrate as a white solid (0.75 g, 67% yield). Estimated isomeric purity (Z-isomer, $^1$H NMR): about 98%. Estimated overall purity ($^1$H NMR): about 90%.

$^1$H-NMR of zuclomiphene (1-A) citrate (CDCl$_3$, 400 MHz, ppm): δ 10.98 (broad s, 3H), 7.20-7.30 (m, 6H), 7.07-7.17 (m, 4H), 6.94-7.03 (m, 4H), 4.25 (broad t, J=5.2 Hz, 2H), 3.32 (broad t, J=4.9 Hz, 2H), 3.04 (broad q, J=7.2 Hz, 4H), 2.56 (ABq, J=15.2 Hz, 4H), 1.15 (broad t, J=7.7 Hz, 6H).

Example 5: Preparation of Zuclomiphene (1-A) Citrate from the Compound of Formula (1-int)

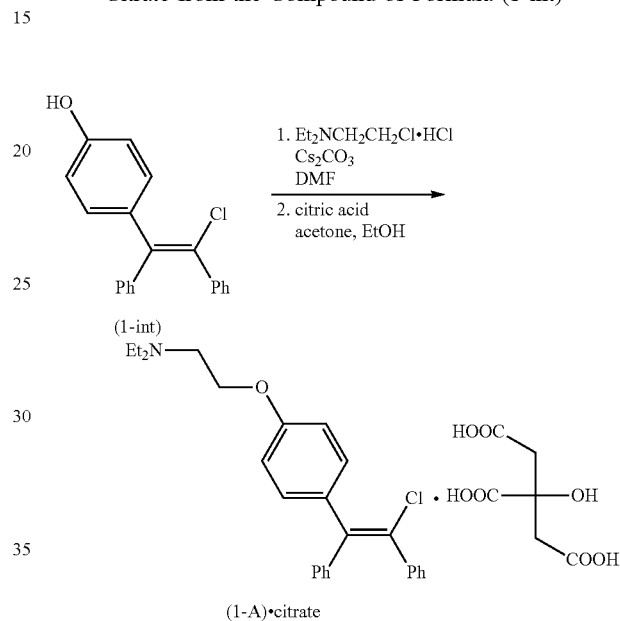

(1-A)·citrate

A mixture of the compound of Formula (1-int) from Example 3 (0.96 g, 3.13 mmol), cesium carbonate (6.13 g, 18.78 mmol), 2-chloro-N,N-diethylethylamine hydrochloride (1.62 g, 9.39 mmol), and dimethylformamide (24 mL) was heated at 70° C. until consumption of starting material. The reaction mixture was then charged into a separatory funnel containing methyl t-butyl ether and water. The organic phase was washed with water three times and 2 wt % hydrochloric acid solution. The organic phase was extracted once more with 2 wt % hydrochloric acid solution and then the combined aqueous phase was washed with methyl t-butyl ether. The pH of the aqueous phase was adjusted to 10 with sodium carbonate and then extracted twice with methyl t-butyl ether. The combined organic phase was filtered through anhydrous sodium sulfate and concentrated in vacuo to afford zuclomiphene (1-A) as a thick brown oil (1.03 g). This material was passed through silica gel (eluent: 5% methanol in ethyl acetate containing 1% triethylamine) to afford zuclomiphene (1-A) as a yellow oil (0.70 g, 55% yield).

This oil (0.70 g) was treated with citric acid (0.33 g, 1.72 mmol) in acetone (5 mL) and ethanol (0.5 mL) to afford zuclomiphene (1-A) citrate as a white solid (0.79 g, 77% yield). Estimated isomeric purity (Z-isomer, $^1$H NMR): about 95%. Estimated overall purity ($^1$H NMR): about 90%.

Example 6: Preparation of Zuclomiphene (1-A) from the Compound of Formula (1-int)

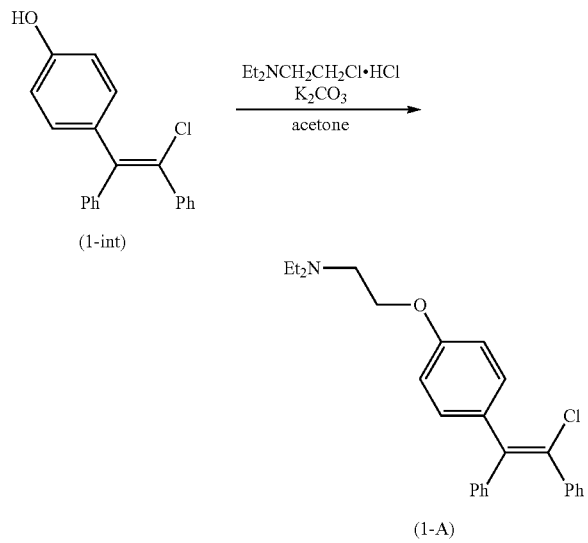

A mixture of the compound of Formula (1-int) as obtained from Example 3 (0.96 g, 3.13 mmol), potassium carbonate (1.73 g, 12.52 mmol) and 2-chloro-N,N-diethylethylamine hydrochloride (1.08 g, 6.26 mmol) in acetone (20 mL) and water (3 mL) was heated to 50° C. for 46 hours. The reaction mixture was concentrated in vacuo to remove acetone then subjected to the work-up procedure described in Example 5 to afford zuclomiphene (1-A) as a brown oil (0.69 g, 54% yield) which solidified on stranding.

Example 7: Preparation of Zuclomiphene (1-A)

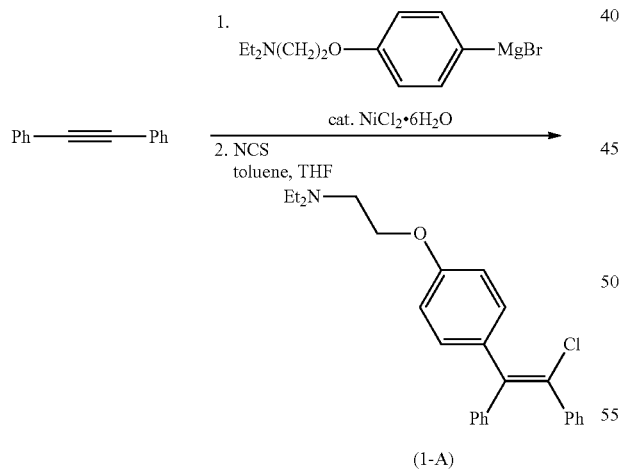

A mixture of magnesium turnings (0.38 g, 15.75 mmol), diisobutylaluminium hydride (0.2 mL) and 2-(4-bromophenoxy)-N,N-diethyl-ethanamide (3.66 g, 13.45 mmol) in tetrahydrofuran (12 mL) was heated to 60° C. and maintained for three hours prior to cooling to room temperature to afford a solution of bromo[4-[2-(N,N-diethylamino)ethoxy]phenyl]magnesium. A dry flask containing a mixture of diphenyl acetylene (1.00 g, 5.61 mmol) and nickel(II) chloride hexahydrate (0.0029 g, 0.021 mmol, 0.4 mol %) was purged with nitrogen gas three times prior to addition of toluene (15 mL), and about half the volume of the prepared bromo[4-[2-(N,N-diethylamino)ethoxy]phenyl]magnesium solution (6.73 mmol). The reaction mixture was then heated to 60° C. and maintained at this temperature until all of the diphenylacetylene was consumed. The reaction mixture was then cooled to room temperature and N-chlorosuccinimide (0.90 g, 6.73 mmol) was charged. Following a period of stirring at room temperature for 5 hours, the reaction mixture was charged into saturated aqueous ammonium chloride solution and extracted with methyl t-butyl ether. The organic phase was acidified with dilute hydrochloric acid and the organic phase was separated. The aqueous phase was washed once with methyl t-butyl ether then made basic with dilute sodium hydroxide. The aqueous phase was extracted three times with methyl t-butyl ether then the combined organic phase was washed with water and brine, filtered through anhydrous sodium sulfate and concentrated to dryness in vacuo to afford crude zuclomiphene (1-A) as a viscous oil (1.48 g). Estimated isomeric purity (Z-isomer, $^1$H NMR): >about 95%.

What is claimed is:
1. A process for the preparation of zuclomiphene (1-A):

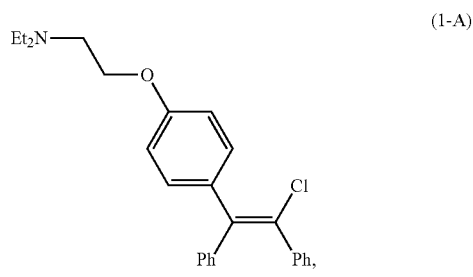

or a salt thereof, comprising:
(i) reacting diphenylacetylene, in the presence of a nickel (II) catalyst, with a compound of Formula (3):

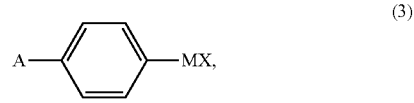

followed by a chlorinating agent,
wherein
A is —OCH$_2$CH$_2$NEt$_2$ or G;
M is zinc or magnesium; and
X is halide;
to provide either zuclomiphene (1-A) when A is —OCH$_2$CH$_2$NEt$_2$ or, when A is G, a compound of Formula (2-A):

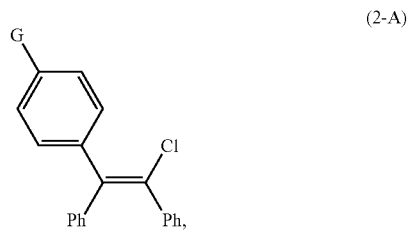

wherein
G is OPG or X$^1$;
PG is an alcohol protecting group;
X$^1$ is halide; and (ii) when A is G, converting the G group in the compound of Formula (2-A) to the —OCH$_2$CH$_2$NEt$_2$ group of zuclomiphene (1-A).

2. The process of claim 1, wherein M is magnesium and X is bromide or chloride.

3. The process of claim 2, wherein the chlorinating agent is selected from the group consisting of chlorine, N-chlorosuccinimide, thionyl chloride, phosphorus trichloride, phosphorus pentachloride, phosphorus oxychloride, hexachloroethane, and 1,3-dichloro-5,5-dimethylhydantoin.

4. The process of claim 3, wherein the chlorinating agent is 1,3-dichloro-5,5-dimethylhydantoin.

5. The process of claim 2, wherein the nickel(II) catalyst is selected from the group consisting of nickel(II) chloride, nickel(II) chloride hexahydrate, nickel(II) bromide, nickel(II) chloride ethylene glycol dimethyl ether complex, nickel(II) bromide ethylene glycol dimethyl ether complex, nickel(II) acetylacetonate, and nickel(II) acetate tetrahydrate.

6. The process of claim 5, wherein the nickel(II) catalyst is nickel(II) chloride hexahydrate.

7. The process of claim 2, wherein the reaction of diphenylacetylene and the compound of Formula (3) is conducted in the presence of a solvent (S1) selected from the group consisting of aromatic hydrocarbons, ethers, and mixtures thereof.

8. The process of claim 2, wherein the reaction of diphenylacetylene and the compound of Formula (3) is conducted at a temperature in the range of about 50° C. to about 80° C.

9. The process of claim 2, wherein the compound of Formula (2-A) is a compound of Formula (2-A1):

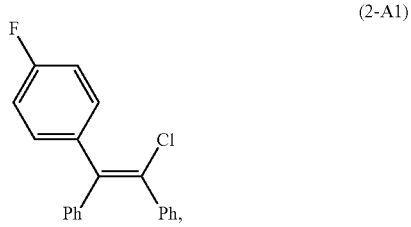 [SMILES: Fc1ccc(/C(=C(\Cl)c2ccccc2)c2ccccc2)cc1]

(2-A1)

and the process of converting the compound of Formula (2-A) to zuclomiphene (1-A), or a salt thereof, comprises reacting the compound of Formula (2-A1) with Et$_2$NCH$_2$CH$_2$OH.

10. The process of claim 9, wherein the reaction of the compound of Formula (2-A1) with Et$_2$NCH$_2$CH$_2$OH is conducted in the presence of a base (B1) that is selected from the group consisting of potassium tert-butoxide, sodium tert-butoxide, sodium hydride, and potassium hydride and a solvent (S3) that is an ether.

11. The process of claim 10, wherein the solvent (S3) is selected from the group consisting of tetrahydrofuran, 2-methyltetrahydrofuran, and 1,4-dioxane and the base (B1) is potassium tert-butoxide.

12. The process of claim 2, wherein the compound of Formula (2-A) is a compound of Formula (2-A3):

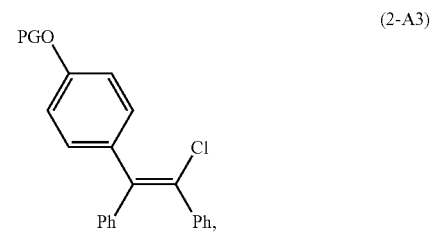

(2-A3)

wherein
PG is an alcohol protecting group,
and the process of converting the compound of Formula (2-A) to zuclomiphene (1-A), or a salt thereof, comprises deprotecting the compound of Formula (2-A3) and alkylating the resulting intermediate with a compound of Formula Et$_2$NCH$_2$CH$_2$LG, or a salt thereof, wherein LG is a leaving group.

13. The process of claim 12, wherein PG is methyl.

14. The process of claim 13, wherein the deprotecting is conducted in the presence of boron tribromide.

15. The process of claim 14, wherein LG is chloride.

16. The process of claim 1, wherein the isomeric purity of zuclomiphene (1-A), or a salt thereof, that is produced is at least about 80%.

17. The process of claim 1, wherein the zuclomiphene (1-A) that is produced is further converted to zuclomiphene (1-A) citrate.

* * * * *